United States Patent
Karl et al.

(10) Patent No.: US 12,162,085 B2
(45) Date of Patent: Dec. 10, 2024

(54) SURGICAL SAW BLADE AND THERMAL MANAGEMENT SYSTEM

(71) Applicant: Stryker Corporation, Kalamazoo, MI (US)

(72) Inventors: Jeffrey Karl, Kalamazoo, MI (US); Girish Karve, Portage, MI (US); Amanda Kingman, Phoenix, AZ (US)

(73) Assignee: Stryker Corporation, Portage, MI (US)

( * ) Notice: Subject to any disclaimer, the term of this patent is extended or adjusted under 35 U.S.C. 154(b) by 981 days.

(21) Appl. No.: 17/260,305

(22) PCT Filed: Jul. 24, 2019

(86) PCT No.: PCT/US2019/043284
§ 371 (c)(1),
(2) Date: Jan. 14, 2021

(87) PCT Pub. No.: WO2020/023664
PCT Pub. Date: Jan. 30, 2020

(65) Prior Publication Data
US 2022/0009013 A1    Jan. 13, 2022

Related U.S. Application Data

(60) Provisional application No. 62/703,944, filed on Jul. 27, 2018.

(51) Int. Cl.
*A61B 17/14* (2006.01)
*B23D 59/04* (2006.01)
*A61B 17/00* (2006.01)

(52) U.S. Cl.
CPC ............ *B23D 59/04* (2013.01); *A61B 17/142* (2016.11); *A61B 2017/00526* (2013.01); *A61B 2017/00831* (2013.01)

(58) Field of Classification Search
CPC ..... A61B 17/14; A61B 17/142; A61B 17/144; A61B 2017/00526; B23D 59/04
See application file for complete search history.

(56) References Cited

U.S. PATENT DOCUMENTS 3,681,846 A   8/1972 Gerber
4,770,067 A   9/1988 Liu et al.
(Continued)

FOREIGN PATENT DOCUMENTS

CA       2050855 A1    3/1992
CN    101674779 A      3/2010
(Continued)

OTHER PUBLICATIONS

Partial Machine-Assisted English Translation for DE 20 2010 004 990 U1 extracted on Jun. 13, 2024, 3 pages.
(Continued)

*Primary Examiner* — Si Ming Ku
(74) *Attorney, Agent, or Firm* — Howard & Howard Attorneys PLLC

(57) ABSTRACT

A surgical saw blade includes a cutting edge, a proximal portion, and a body portion. The cutting edge has teeth and is substantially formed of a first material having a first thermal conductivity. The proximal portion includes a blade hub. The body portion connects the cutting edge and the proximal portion and includes a thermal transit core formed of a second material having a second thermal conductivity at least twice the first thermal conductivity. The core has a at least two longitudinally extending, core surfaces. The body portion includes at least two longitudinally extending flanking members disposed over the longitudinally extending core surfaces.

24 Claims, 11 Drawing Sheets

(56) References Cited

U.S. PATENT DOCUMENTS

| | | | |
|---|---|---|---|
| 5,002,555 A * | 3/1991 | Petersen | A61B 17/144 83/835 |
| 5,308,311 A | 5/1994 | Eggers et al. | |
| 6,022,353 A | 2/2000 | Fletcher et al. | |
| 7,998,158 B2 | 8/2011 | Fletcher et al. | |
| 8,142,425 B2 * | 3/2012 | Eggers | A61B 18/082 606/29 |
| 8,628,534 B2 | 1/2014 | Jones et al. | |
| 9,050,124 B2 | 6/2015 | Houser | |
| 10,211,705 B2 | 2/2019 | Hayashi | |
| 2003/0199880 A1 * | 10/2003 | Meckel | A61B 17/142 606/82 |
| 2004/0243136 A1 * | 12/2004 | Gupta | B23D 61/121 606/82 |
| 2005/0203567 A1 | 9/2005 | Linder et al. | |
| 2006/0016315 A1 | 1/2006 | Zorich et al. | |
| 2008/0210212 A1 | 9/2008 | Baratta | |
| 2009/0312762 A1 | 12/2009 | Boykin | |
| 2011/0089220 A1 | 4/2011 | Ingmanson et al. | |
| 2017/0027586 A1 | 2/2017 | Ferro | |
| 2018/0125503 A1 | 5/2018 | Sidebotham et al. | |
| 2020/0001494 A1 * | 1/2020 | Gisler | B23D 61/006 |

FOREIGN PATENT DOCUMENTS

| | | |
|---|---|---|
| CN | 102098970 A | 6/2011 |
| DE | 202010004990 U1 | 8/2010 |
| DE | 102010014917 A1 | 10/2011 |
| JP | S58109221 A | 6/1983 |
| JP | H1156867 A | 3/1999 |
| JP | 2004001134 A | 1/2004 |
| JP | 2007532253 A | 11/2007 |
| JP | 2008528242 A | 7/2008 |
| JP | 2016140150 A | 8/2016 |

OTHER PUBLICATIONS

English language abstract and machine-assisted English Translation for JPS 58-109221 A extracted from espacenet.com database on May 30, 2023, 4 pages.

English language abstract and machine-assisted English Translation for JPH 11-56867 A extracted from espacenet.com database on May 30, 2023, 10 pages.

English language abstract and machine-assisted English Translation for JP 2004-001134 A extracted from espacenet.com database on May 30, 2023, 4 pages.

English language abstract for JP 2007-532253 A extracted from espacenet.com database on May 30, 2023, 2 pages.

English language abstract for JP 2008-528242 A extracted from espacenet.com database on May 30, 2023, 2 pages.

English language abstract for JP 2016-140150 A extracted from espacenet.com database on May 30, 2023, 2 pages.

International Search Report for Application No. PCT/US2019/043284 dated Dec. 12, 2019, 3 pages.

English language abstract for CN 101674779 A extracted from espacenet.com database on Dec. 3, 2023, 2 pages.

English language abstract and machine-assisted English Translation for CN 102098970 A extracted from espacenet.com database on Dec. 3, 2023, 19 pages.

English language abstract and machine-assisted English Translation for DE 10 2010 014 917 A1 extracted from espacenet.com database on Dec. 3, 2023, 9 pages.

\* cited by examiner

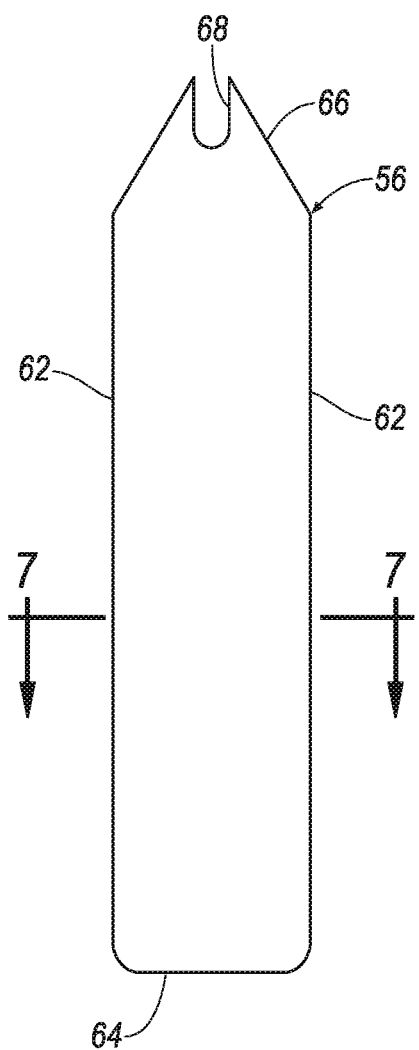
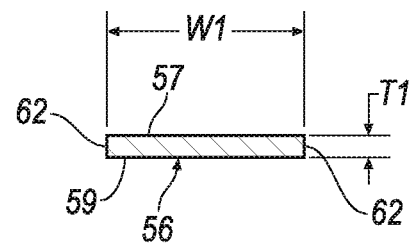
FIG. 6
FIG. 7

SURGICAL SAW BLADE AND THERMAL MANAGEMENT SYSTEM

CROSS REFERENCE TO RELATED APPLICATION

This application claims priority to and all advantages of International Patent Application No. PCT/US2019/043284, filed Jul. 24, 2019, which claims priority to and the benefit of U.S. Provisional Patent Application No. 62/703,944, filed on Jul. 27, 2018, each of which is hereby incorporated herein by reference in its entirety.

BACKGROUND

A powered surgical saw system having a surgical saw blade may be used to remove tissue, including bone and cartilage during a surgical procedure. Powered surgical saw systems, including surgical saw blades, beneficially aid surgeons in performing orthopedic surgery. There is a need for an improved surgical saw blade and surgical saw system that facilitates improved surgical precision and efficiency.

BRIEF DESCRIPTION OF THE DRAWINGS

FIG. 6 is a top view of an example thermal transit core of the saw blade of FIG. 3.

FIG. 7 is a sectional view of the thermal transit core of FIG. 6 taken in the direction of arrows 7.

DETAILED DESCRIPTION

Figure 1:
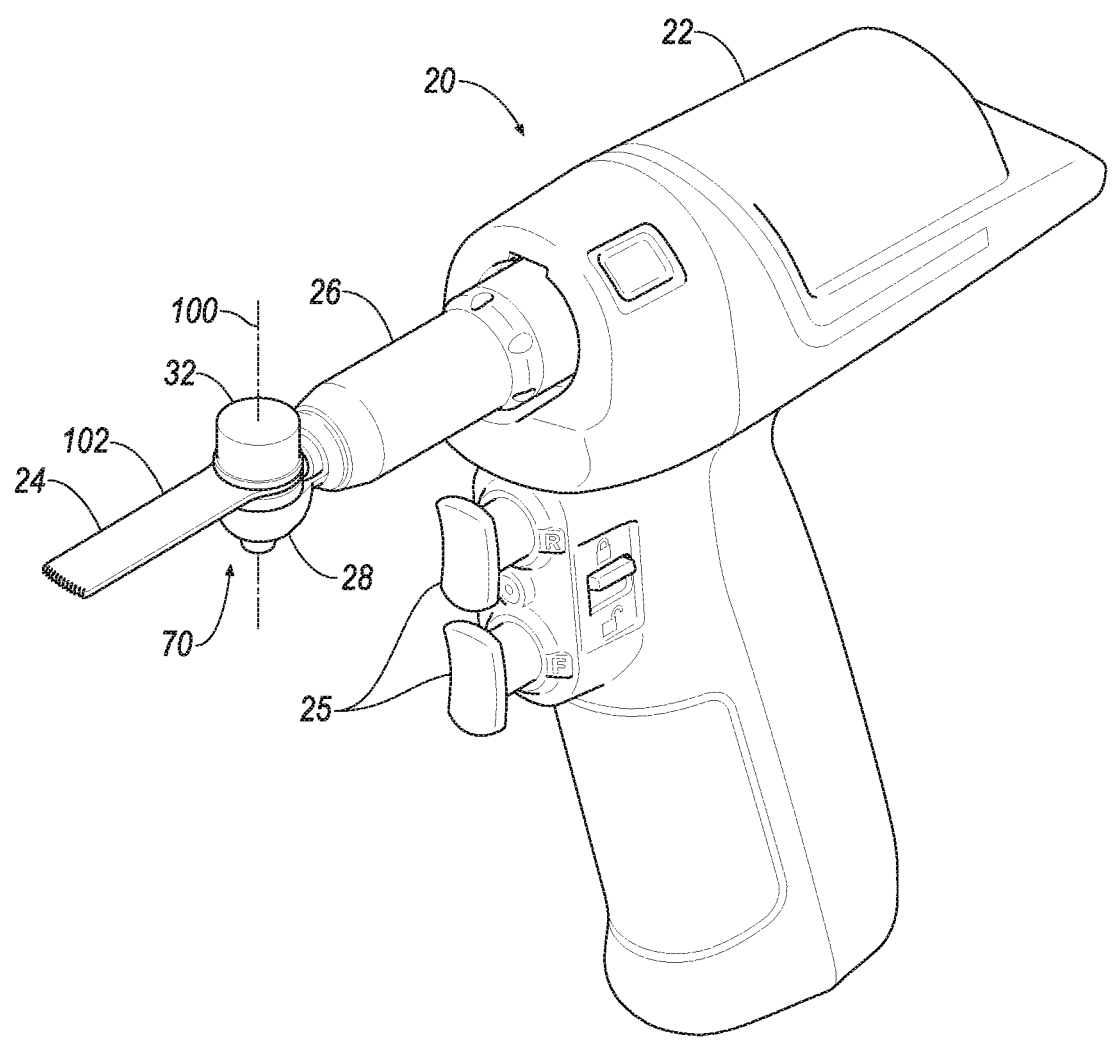
FIG. 1 illustrates an example powered surgical saw system.

A disclosed saw blade comprises a thermally conductive core and beneficially allows cutting at a lower blade temperature than known blades. The blade temperature may be further reduced with the use of a supplemental heat sink at a blade mount.

A surgical saw blade includes a cutting edge, a proximal portion, and a body portion. The cutting edge has a plurality of teeth and is substantially entirely formed of a first material having a first thermal conductivity. The proximal portion includes a blade hub. The body portion is disposed between and connects the cutting edge and the proximal portion. The body portion includes a thermal transit core formed of a second material having a second thermal conductivity at least twice the first thermal conductivity. The core has at least two opposed longitudinally extending first core surfaces extending across a width of the core. The body portion includes at least two opposed longitudinally extending first flanking members respectively disposed over the longitudinally extending first core surfaces.

The cutting edge may be formed of steel and the longitudinally extending flanking members may be formed of steel.

The cutting edge may be formed of steel and the proximal portion may be formed substantially entirely of steel.

The cutting edge may be disposed at a distal end of the blade. The cutting edge may be formed of steel.

The cutting edge may be disposed at a distal end of the blade. The saw blade may be substantially symmetrical about a longitudinal axis extending from the blade hub to the teeth.

Steel sheets may be disposed over the first and second surfaces of the thermal transit core to provide the flanking members.

The cutting edge may be formed of steel. A pair of opposed second flanking members may be formed of steel. The second flanking members may be connected to the first flanking members and extend along each of two opposed second surfaces of the thermal transit core extending across a thickness of the thermal transit core.

The cutting edge may be located on a distal end of the saw blade opposite the blade hub. The body portion may comprise more than half of a length of the saw blade. The surgical saw blade, including the proximal portion and the cutting edge and the body portion, is substantially planar and of a substantially constant thickness.

The thermal transit core may substantially comprise copper.

The thermal transit core may substantially comprise aluminum.

A surgical saw blade thermal management system includes a surgical saw blade and a blade mount. The surgical saw blade includes a cutting edge, a proximal portion and a body portion. The cutting edge includes a plurality of teeth substantially entirely formed of a first material having a first thermal conductivity. The proximal portion includes a blade hub. The body portion is disposed between and connects the cutting edge and the proximal portion, and includes a thermal transit core formed of a second material. The second material has a second thermal conductivity at least twice the first thermal conductivity. The thermal transit core has at least two opposed longitudinally extending first core surfaces extending across a width of the core. The body portion includes at least two longitudinally extending flanking members disposed over the longitudinally extending first core surfaces. The blade mount is in receipt of the blade hub of the blade and is connected to a saw hand piece. The blade mount includes a heat sink.

The heat sink may be a passive heat sink.

The heat sink may be an active heat sink.

The heat sink may be an electrically actuable active heat sink.

The thermal transit core of the system may substantially comprise copper.

The thermal transit core may substantially comprise copper.

A method of making a surgical saw blade includes the steps of forming layers of a blank sheet assembly, forming the blank sheet assembly, cutting a plurality of saw blade blanks, forming a blade hub, and forming cutting teeth. The blank sheet assembly includes a substantially planar first sheet of steel, a substantially planar second sheet of steel, and an intermediate layer disposed between the first sheet and the second sheet. The substantially planar first sheet is formed of steel and is of a first thickness and has a first planar area. The second sheet is formed of steel and has a second planar area substantially equal to the first planar area and has a second thickness substantially equal to the first thickness. The intermediate layer includes both steel incorporated into cutting edges and a second material having a thermal conductivity greater by at least a factor of two than the thermal conductivity incorporated into a thermal transit core in blades formed. The first and second sheets are fixed to opposite sides of the intermediate layer to form a blank sheet assembly. A plurality of saw blade blanks are cut from the blank sheet assembly with each blank having a thermal transit core formed of the second material and a cutting edge formed of steel. A blade hub is formed in a proximal end of the blade blank. Cutting teeth are formed on the cutting edge of the blade blank.

The steel of the intermediate layer may be provided as a third sheet of steel including a plurality of regularly disposed pockets of a predetermined shape and size formed therein. The second material may be provided as a plurality of thermal transit cores of substantially the same size and shape as the pockets. The step of disposing the thermal transit cores in the pockets of the third sheet may also be included.

The steel of the intermediate layer may also comprise at least part of the proximal end.

The first and second steel sheets may be welded to the steel of the intermediate layer.

The thermal transit cores may substantially comprise copper.

A surgical saw system includes a hand piece and a blade mount. The blade mount is connected to a saw hand piece. The blade mount is connected to a heat sink.

The heat sink may be a passive heat sink.

The heat sink may be a passive heat sink 32 with a plurality of cooling fins 74 extending from a heat sink base 76. The heat sink base may be connected to the blade mount.

The heat sink may be an active heat sink.

The heat sink may be an electrically actuable active heat sink.

The surgical saw system may include a fan positioned to blow air across the heat sink.

Relative orientations and directions (by way of example, upper, lower, bottom, rearward, front, rear, back, outboard, inboard, inward, outward, lateral, left, right, proximally, distally) are set forth in this description not as limitations, but for the convenience of the reader in picturing at least one embodiment of the structures described. Here, "proximally" is understood to mean towards the surgeon holding a saw hand piece 22, away from the surgical site to which a surgical saw blade 24 is applied. "Distally" is understood to mean away from the surgeon and towards the site to which the saw blade 24 is applied.

The elements shown may take many different forms and include multiple and/or alternate components and facilities. The example components illustrated are not intended to be limiting. Additional or alternative components and/or implementations may be used. Further, the elements shown are not necessarily drawn to scale unless explicitly stated as such.

Figure 2:
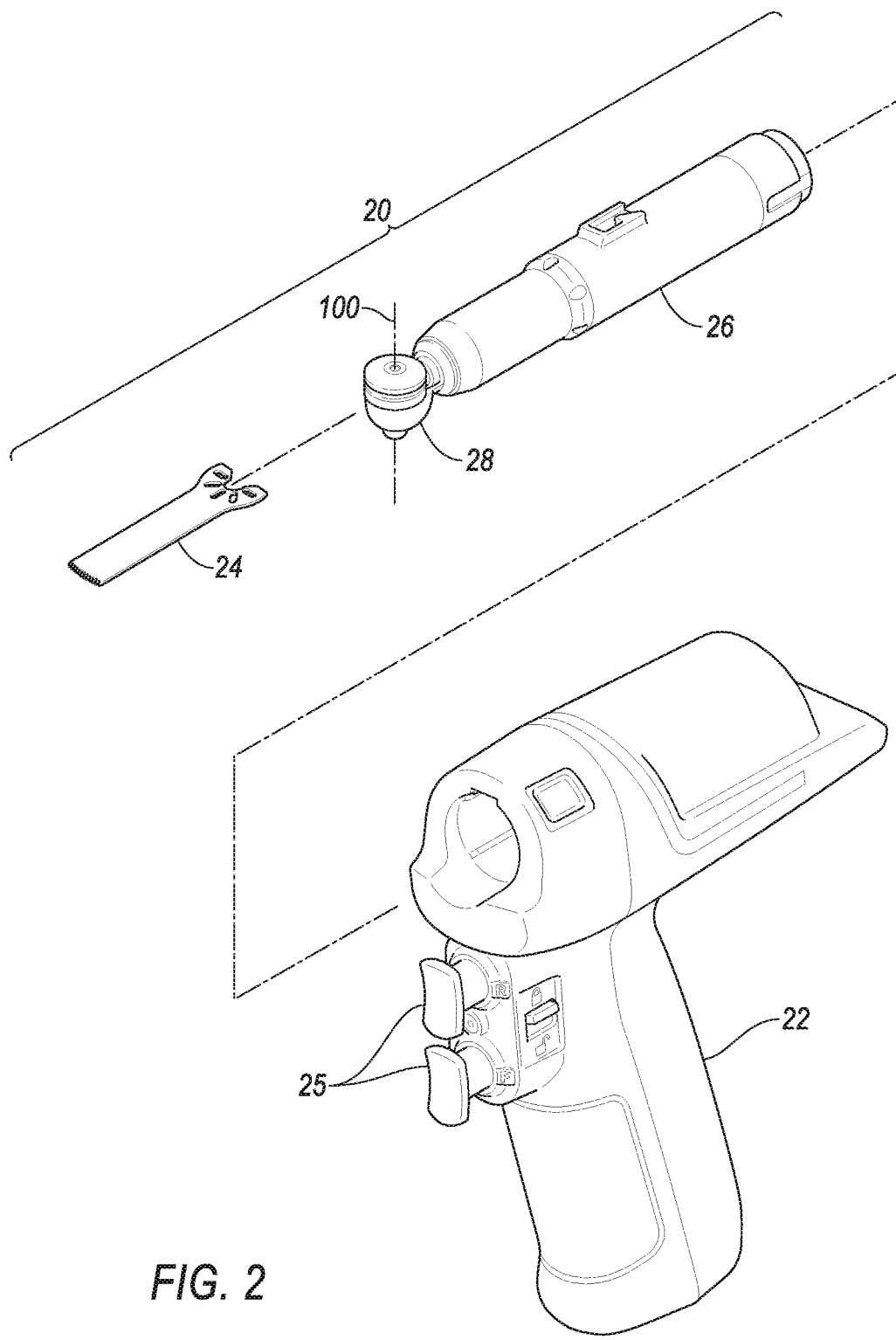
FIG. 2 is an exploded view of the example surgical saw system of FIG. 1.

As illustrated in FIGS. 1 and 2, a powered surgical saw system 20 includes the saw hand piece 22, a pistol-type hand piece 22 being shown, that drives a surgical saw blade 24. Other configurations for the hand piece, e.g., a pencil-type, may be employed. The saw hand piece 22 may include a driving motor (not shown) for operably moving the saw blade, a power source for energizing the driving motor, e.g., a battery or alternating current electrical power from a wall socket, an operator input control element that may be in the form of a finger-responsive trigger 25, and a controller (not shown) for regulating the power supplied to the motor responsive to a displacement of the operator input control element.

The surgical saw blade 24 is selectively connected to the hand piece 22 by a saw adapter 26 of the hand piece 22. The saw adapter 26 may include a blade mount 28 having an interface compatible with an example blade hub 30, 30' of the saw blade 24 of a shape shown in FIG. 3, or alternatively that of FIG. 5. The referenced saw adapter 26 may be selectively removable from the rest of the hand piece 22 as illustrated in FIG. 2. An example hand piece including such an interface is commercially available as part of the Stryker F1™ Small Bone Power System. A saw blade heat sink 32, 32', described in more detail below and illustrated in FIGS. 8A and 8B, may be incorporated into or joined with the blade mount 28, and may also comprise part of a surgical saw blade thermal management system 70, also described in more detail below.

Figure 3:
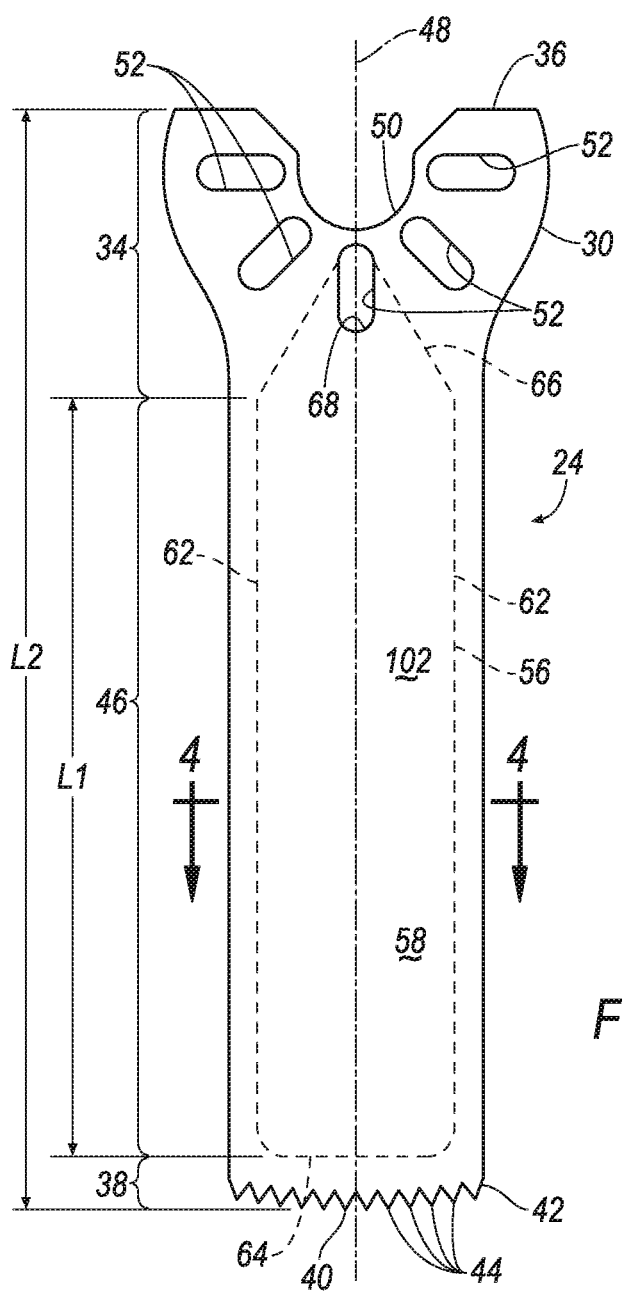
FIG. 3 is a top view of an example surgical saw blade of the example saw system of FIGS. 1 and 2.
Figure 4:
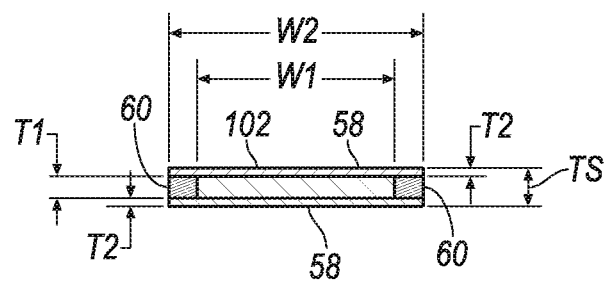
FIG. 4 is a sectional view of the saw blade of FIG. 3 taken in the direction of arrows 4.

FIGS. 3 and 4 show the example surgical saw blade 24 in detail. A proximal portion 34 of the blade 24, disposed at a proximal end 36 of the blade 24, includes the blade hub 30. A distal portion 38 of the blade 24, disposed at a distal end 40 of the blade 24 opposite the proximal end 36 and blade hub 30, includes a cutting edge 42. The cutting edge 42 may include a plurality of cutting teeth 44. A body portion 46 is disposed between and connects the proximal portion 34 and the cutting edge 42 of the distal portion 38. A longitudinal axis 48 extends from the proximal end 36 to the distal end 40, substantially bisecting the blade 24. The saw blade 24 may be substantially symmetrical about the axis 48, with opposing sides of the blade 24 across the axis 48 being substantially a mirror image of the other. The blade 24 and its body portion 46, as shown in FIGS. 3 and 4, are substantially planar and may be of a substantially constant thickness. The blade may include reinforcement features that may be in the form of a surface discontinuity, e.g., a raised rib or ribs.

An alternative blade for use as a reciprocating saw, not illustrated, may have a cutting edge extending on a side of the blade parallel to the longitudinal axis 48. Yet alternatively, the body portion 46 may have a non-planar shape, e.g., a curved shape, with teeth at a distal end, allowing the blade's use for removal of an artificial acetabular cup. The body portion 46 may have a length L1 comprising more than half a length of the saw blade L2. An example length L1 may be 24 millimeters ("mm") and an example length L2 may be 36 mm.

The distal portion 38, and thus the cutting edge 42 and the teeth 44, may all be formed of a first material that has a first yield strength and has a first thermal conductivity. The first material may also be a biocompatible material. As used herein, biocompatible means that the so-described material or feature is not toxic or otherwise harmful to human tissue. An example biocompatible first material is stainless steel, type 440. Subsequent references to steel and to stainless steel and to series 300 and 400 stainless steel are inclusive of stainless steel, type 440. A representative range of yield strength of stainless steel is from 450 to 1900 megapascals (MPa). A representative range of values of thermal conductivity of stainless steel is 12 to 45 Watts per meter-Kelvin (W/mK). Other materials, e.g., other high carbon stainless steels (e.g., 300 or 400 series stainless steel), tungsten carbide, or titanium, may be used. The teeth 44 are illustrated as being co-planar with the body portion 46. With the teeth 44 so oriented, the saw blade 24, when held in a planar orientation, cuts a kerf (not shown) having a thickness substantially equal to a saw blade thickness TS of the saw blade 24. The thickness TS of the saw blade 24 is illustrated in FIG. 4. An example thickness TS is 0.38 mm. Alternatively, the teeth 44 may have tips angled away from a plane of the body, allowing the teeth 44 to cut a kerf having a width greater than the thickness TS of the saw blade 24.

Figure 5:
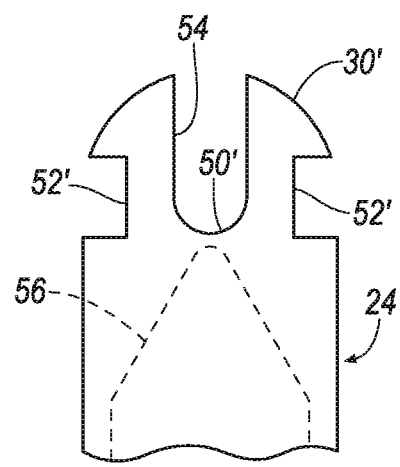
FIG. 5 is a broken-out top view of an alternative example blade having an alternative blade hub.

The proximal portion 34 may be formed of the same material as the distal portion 38 (i.e., the first material). One example proximal portion 34 includes the blade hub 30 that includes mounting features, e.g., an engagement arc 50 and a plurality of position-retention slots 52. The engagement arc 50 aids in establishing a fore-aft position, i.e., a distal-proximal position of the blade 24 in the blade mount 28. The position-retention slots 52 may receive interface elements (not shown) of the blade mount 28 that retain the blade 24 in a rotative position relative to the blade mount 28. One alternative blade hub 30' is illustrated in FIG. 5. An engagement arc 50' is provided at a bottom of a receiving slot 54. Opposed retention slots 52' of feature 30' are engaged by compatible interface elements (not shown). The described hubs 30, 30' and their associated mounting features are merely exemplary and not intended to be comprehensive, as many alternatives are well known and in commercial use. Alternatively, the proximal portion 34 may share a laminar-type construction used for the body portion 46, such laminar-type construction being described below.

The body portion 46 includes a thermal transit core 56 formed of a second material, e.g. copper, aluminum, composites, example composite materials including diamond, synthetic diamond and carbon nanotubes, having a second thermal conductivity greater than, and at least twice the first thermal conductivity. However, materials having a high thermal conductivity may have a much lower yield strength than materials well suited to providing the cutting edge 42 and the teeth 44 thereof. For example, a representative value of thermal conductivity of copper is 386 W/mK, more than 8 times the above-cited thermal conductivity of stainless steel. But, a representative yield strength of copper, at 70 MPa, is much lower than that of stainless steel. And a representative value of thermal conductivity of aluminum is 204 W/mK, more than four times the above-cited thermal conductivity of stainless steel. But, a representative yield strength of aluminum at 95 MPa is also much lower than that of stainless steel. Accordingly, the body portion 46 may also include a pair of, i.e., two, opposed horizontal flanking members 58 and/or a pair of opposed vertical flanking members 60. The flanking members 58, 60 may be made of a stiffer material than the material of the thermal transit core 56, e.g., the same material as the distal portion 38 or the proximal portion 34, such as stainless steel. Such flanking members 58, 60 may aid the transmission of a cutting force from the blade mount 28 to the teeth 44 by providing the body portion 46 with a greater lateral bending stiffness in a cutting mode of operation than would be possible without the flanking members 58, 60. The flanking members 58, 60 may extend longitudinally, i.e., extend in the direction of the longitudinal axis 48, from the proximal portion 34 across the body portion 46 to the distal portion 38.

The labels horizontal and vertical are used consistent with the accompanying drawings only for the convenience of orienting the reader of this description. The horizontal flanking members 58 may alternatively be referred to as, for example, the first flanking member, and the vertical flanking members 60 may be referred to as, for example, the second flanking members.

The core comprises a plurality of surfaces which may include an upper horizontal surface 57, a lower horizontal surface 59, and two vertical surfaces 62. One of the horizontal flanking members 58, when incorporated, may be disposed across the upper horizontal surface 57 of the core 56, and another of the horizontal flanking members 58 may be disposed across the lower horizontal surface 59 of the core 56. The upper horizontal surface 57 and the lower horizontal surface 59 of the core 56 each extend longitudinally, consistent with FIGS. 6 and 7, an entire length of the core 56. The two horizontal surfaces 57, 59 are opposed to each other. The upper horizontal surface 57 and the lower horizontal surface 59 as illustrated in FIG. 7 are connected with each other on opposed sides by the two oppositely disposed vertical surfaces 62 of the core 56. The vertical surfaces 62 also extend longitudinally along the length of the core 56. One of the vertical flanking members 60, when incorporated, may be disposed across one of the vertical surfaces 62 of the core 56, and another of the vertical flanking members 60 may be disposed across the opposed vertical surface 62 of the core 56 as shown in FIG. 4. The core 56 may be alternatively formed without discreet vertical surfaces 62, by, for example, providing the core with a slightly convex cross section by providing one or both of the horizontal surface 57, 59 with a radius, allowing surfaces 57, 59 to join to each other directly without an intermediate surface.

As with the context of the flanking members 58 and 60, the labels horizontal and vertical, as well as upper and lower, are used consistent with the accompanying drawings only for the convenience of orienting the reader of this description. The horizontal surfaces 57 may alternatively be referred to as the first surfaces, and the vertical surfaces 62 may be referred to as the second surfaces.

A width W1 of the core 56 as shown in FIG. 7 may be equal to a full width W2 of the saw blade 24 and the width W2 of the opposed horizontal flanking members 58. Or, as may be seen in FIG. 4, a width W1 of the core 56 may be less than a width W2 of the saw blade 24 and the horizontal flanking members 58 to accommodate the inclusion of the vertical flanking members 60 against the vertical surfaces 62. An example width W1 may be 7 mm and an example width W2 may be 9 mm. The width W2 may be greater than the width W1 to allow the vertical flanking members 60 to be disposed against each of the opposed vertical surfaces 62.

A distal edge 64 of the core 56 is engaged by the distal portion 38 of the blade 24. A proximal end 66 of the core 56 may extend into the blade hub 30 to aid in a transfer of heat from the teeth 44 as described in more detail below. The thermal transit core 56 is illustrated in FIG. 6 as including a positioning slot 68 employed in association with the illustrated blade hub 30. The core 56 may be formed without the positioning slot 68, and may have the slot 68 formed as part of the saw blade's assembly operation as described in more detail below. Alternatively, use of the blade hub 30' shown in FIG. 5 would not require the provision of one of the positioning slots 68 in the core 56.

The vertical flanking members 60 and inner parts of the proximal portion 34 and the distal portion 38 may be formed as an integral unit, as described in greater detail below.

There may be varying degrees of overlap of the core 56 with the blade hub 30, 30' that accommodate both a desired ability of the blade hub 30, 30' to transmit force through the body portion 46 and to the teeth 44 and to transfer heat energy through the blade hub 30, 30'. Additional variations in shape besides those illustrated in FIGS. 3 and 5 may be possible, e.g., extending the core 56 to be under substantially all of the blade hub 30, 30'. So extending the core increases the area of the core 56 under the blade hub 30, 30' and in proximity with the blade mount 28 and thereby facilitates more rapid heat transfer from the blade 24 to the blade mount 28.

Figure 15:
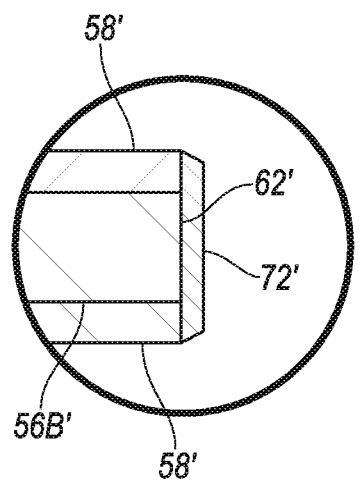
FIG. 15 is an enlarged sectional view of the portion of the blade of FIG. 14 in circle 15.

The body portion 46 may be provided with a biocompatible surface. When the core 56 is formed of a non-biocompatible material, e.g., substantially pure copper, a layer forming the biocompatible surface may be provided by disposing the flanking members 58, 60 over the upper horizontal surface 57, over the lower horizontal surface 59 and over the vertical surfaces 62 of the core 56. The biocompatible surface may alternatively be provided by alternative types of layers, e.g., integrally formed layers and coatings as illustrated in FIG. 15 and described below. The layer 72' may be integral with the thermal transit core 56. For example, if the core 56 is formed of aluminum, the biocompatible surface layer may be a layer of aluminum oxide, or an anodized aluminum layer. Alternatively, the layer 72' of biocompatible material may be provided with other materials and coating methods, e.g., deposition of polymeric coatings, electro-plating of biocompatible metals, e.g., gold, deposition of titanium nitride.

Figure 8A:
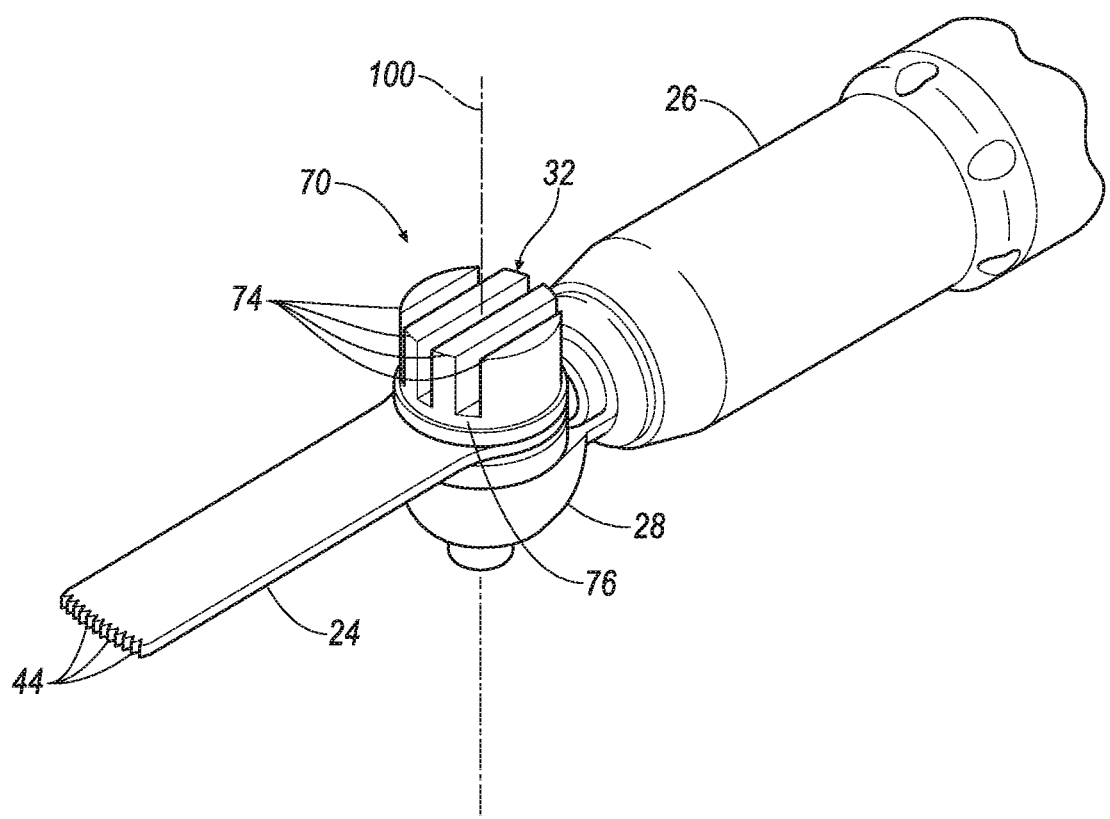
FIG. 8A is a perspective view of an example saw blade thermal management system of the example saw system of FIGS. 1 and 2 with an example passive heat sink.
Figure 8B:
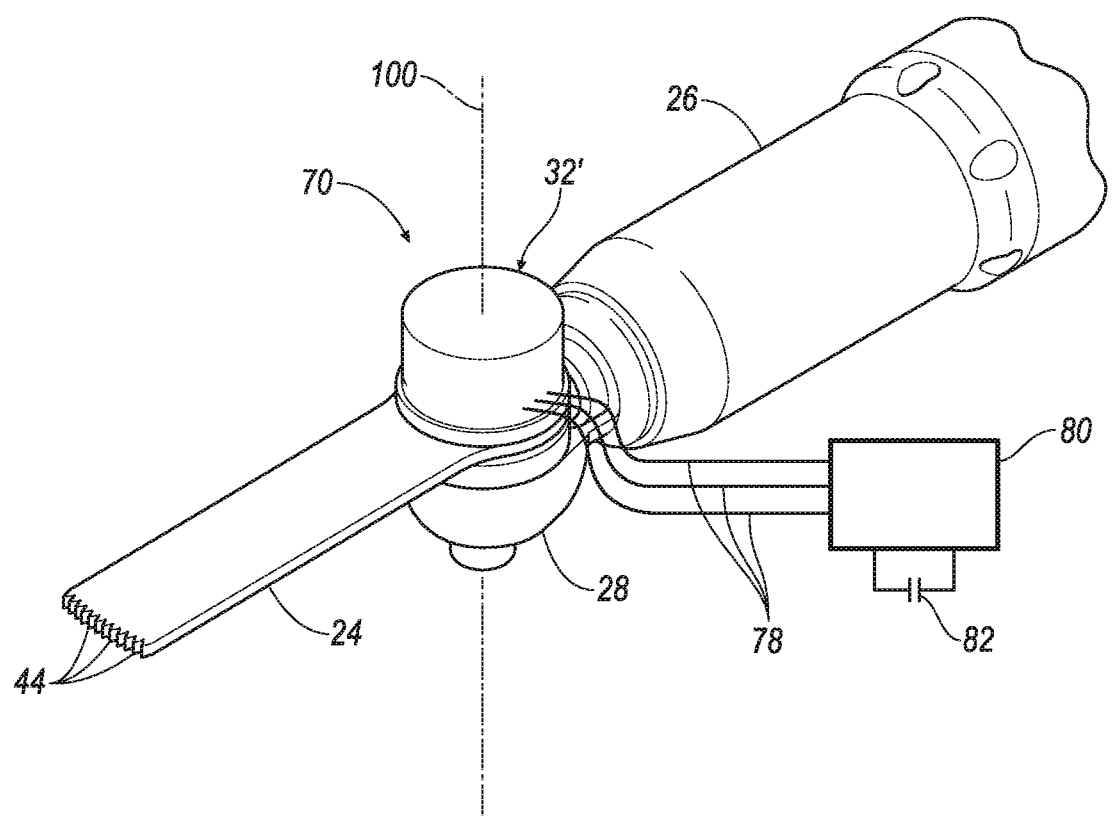
FIG. 8B is a combined perspective and schematic view of an example saw blade thermal management system of the example saw system of FIGS. 1 and 2 with an example active heat sink.

The surgical saw blade 24 may comprise part of the thermal management system 70. The thermal management system 70 may include the supplemental heat sink 32, 32' disposed over and integrated into the blade mount 28 as illustrated in FIGS. 8A and 8B. The heat sink 32, 32' is identified as a supplemental heat sink 32, 32', as the blade mount 28 may have an inherent capacity to act as a heat sink. The heat sink 32, 32' may be a passive heat sink 32 or an active heat sink 32'. The heat sink 32, 32' is connected to the surgical saw blade 24 through the blade hub 30 of the blade 24 and the blade mount 28. Alternatively, the heat sink 32, 32' may be connected to the blade 24 by an intermediate heat transport path, not shown. The thermal management system 70 comprise the heat sink 32, 32' and may be independent of the blade 24 and the blade type, and may be used with a conventional saw blade with beneficial effect.

FIG. 8A shows an example passive heat sink 32 with a plurality of cooling fins 74 extending from a heat sink base 76. Heat is transferred from the blade 24 to the base 76 of the heat sink 32. Heat radiates from the fins 74 into the surrounding air. The heat sink 32 is identified as "passive" as it requires no supplemental power to perform is function of absorbing and dissipating heat energy.

FIG. 8B shows an example active heat sink 32' as might be provided with an electrically actuable active heat sink, e.g., a Peltier cooler 32'. The active heat sink 32' may be disposed over the blade mount 28. A plurality of wires 78 may be used to connect the active heat sink to an electronic controller 80 for power, and to communicate a feedback signal from a temperature sensor (not shown) at the blade mount 28 to the controller 80. Power from an electrical power source 82, e.g., a battery, may be communicated by the controller 80 to the Peltier cooler 32' or other active heat sink. The controller 80 and the power source 82 may be the same as the controller and power source incorporated into the hand piece 22. Although not illustrated, such communication of power and signals may be done wirelessly. The heat sink 32' is identified as "active" as it employs supplemental power, e.g., electrical power, to perform is function of absorbing and dissipating heat energy.

An alternative active heat dissipation mechanism (not illustrated) may supplement the otherwise passive heat sink 32 with a fan (not shown) positioned to blow air across the fins 74. The fan may be electrically responsive to an electronic controller.

One example method including a plurality of steps to fabricate the saw blade 24 is described below and illustrated in FIGS. 9 through 12C.

A sufficiently strong material, e.g., series 300 or 400 stainless steel, tungsten carbide, or titanium, is identified and selected for use as the first material for use in forming the distal portion 38, and thus the cutting edge 42 and the teeth 44, and the flanking members 58, 60. The first material may also be a biocompatible material.

A thermally conductive material having a significantly higher thermal conductivity than the first material is identified and selected for use as the second material for the thermal transit cores 56. Suitable materials for the thermal transit cores 56 include but are not limited to copper and aluminum. "Copper" as used herein includes pure copper and copper-based alloys. Likewise, "aluminum" as used herein includes pure aluminum and aluminum-based alloys. Alternative thermally conductive materials may include other materials, compounds, composites and laminates. For example, the second material may include alternating layers of aluminum and copper, or yet alternatively may include a fine mesh grid of steel with copper filling the voids in the mesh disposed between the cutting edge 42 and the proximal portion 34. Such example are illustrative and not intended to be comprehensive.

One example method of making the saw blades 24, illustrated in FIGS. 9 through 12C, includes the step of forming a laminate in the form of a blade blank sheet assembly 96 including the first material and the second material, with a first layer 92, and a second layer 90, and an intermediate layer disposed in-between.

The first layer 92 in the form of a substantially planar first sheet 92 of the first material having an example thickness T2 of 0.08 mm is provided. The first sheet 92 has a first planar area A1 that may depend on the available manufacturing equipment suitable for forming and processing the blank sheet assembly 96. The second layer 90 in the form of, i.e., comprises, a substantially planar second sheet 90 of the first material, also having an example thickness T2 of 0.08 mm is provided. The second sheet 90 has a second planar area substantially equal to the first planar area A1.

The intermediate layer may include both the first material, e.g., stainless steel, for incorporation therein, and the second material, e.g., copper, for incorporation therein. In one example method, the first material for the intermediate layer may be provided as a third sheet 84 of the first material that may be of the first planar area A1. The intermediate layer may also include a plurality of cores 56 formed of the second material.

Figure 9:
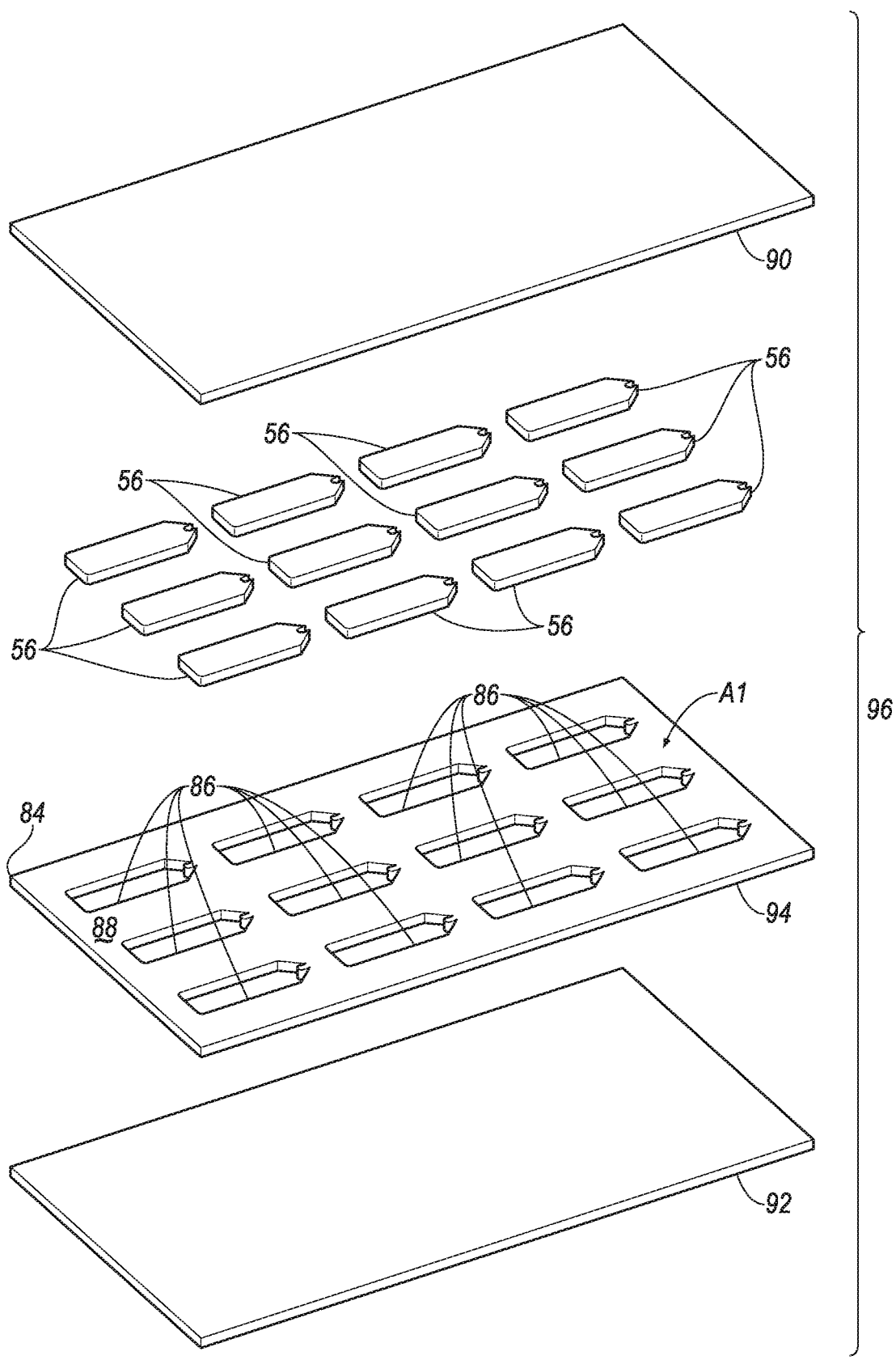
FIG. 9 is an exploded view of an example blank sheet assembly for use in the fabrication of the example saw blade of FIG. 4.
Figure 10:
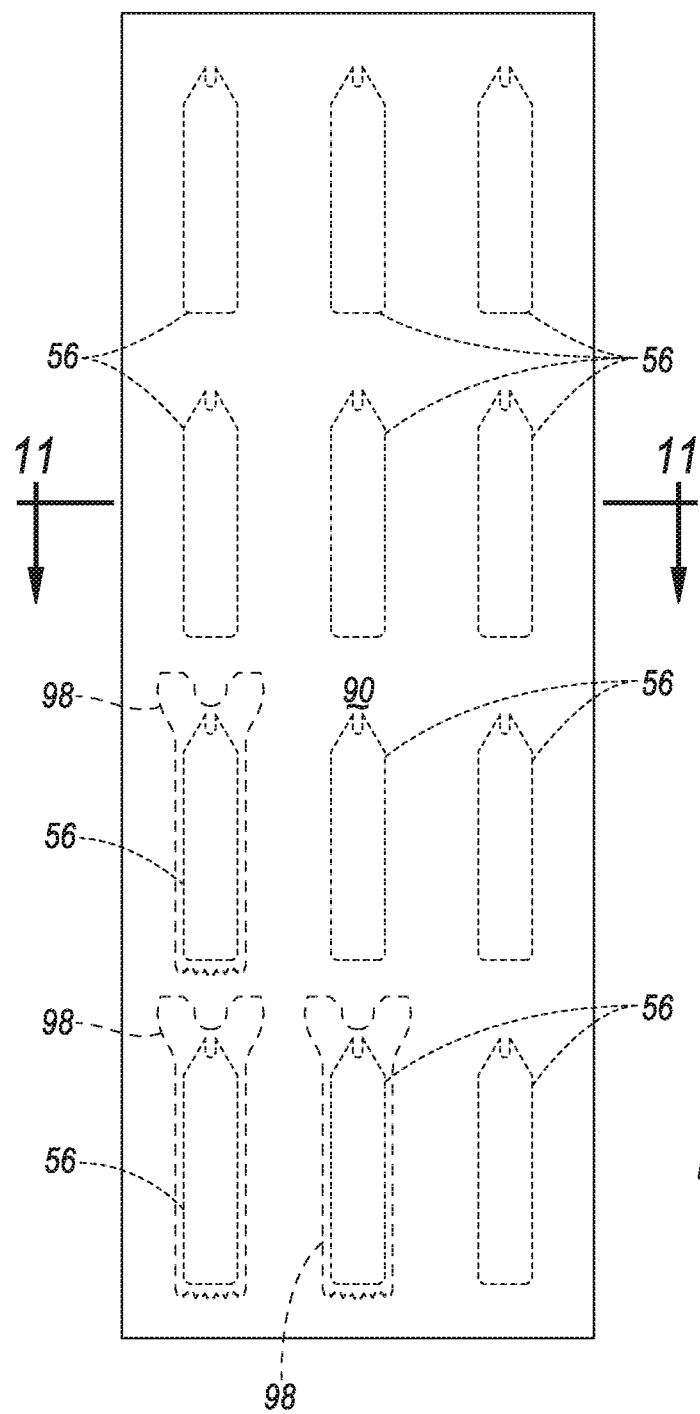
FIG. 10 is a top view of the example blank sheet assembly of FIG. 9 in an assembled condition.
Figure 11:
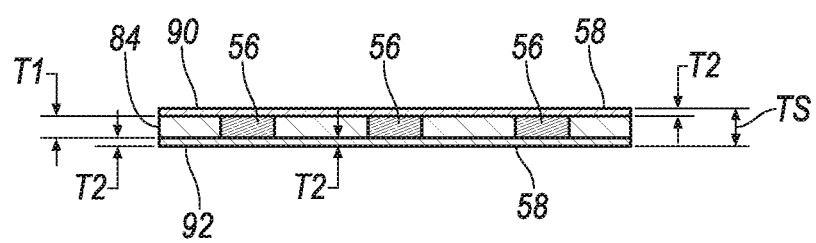
FIG. 11 is a sectional view of the example blank sheet assembly of FIG. 10 taken in the direction of arrows 11.

The first planar area A1 of the third sheet 84 is sufficiently large to accommodate a fabrication of a predetermined number of saw blades 24, with twelve saw blades 24 being an example number illustrated in FIGS. 9 and 10. A plurality of pockets 86, one for each of the blades 24 to be formed, are formed in the third sheet 84 in anticipation of receiving thermal transit cores 56 therein. The example pockets 86 are of a predetermined size, complementary in size and shape to the thermal transit cores 56, with the pockets 86 being of substantially the same size and shape as the cores 56. Accordingly, the cores 56 are of substantially the same size and shape as the pockets 86. By way of example, the third sheet 84 may have a thickness of 0.23 mm. The orientation of the pockets 86 may be such that the utilization of the sheet 84 to produce blades 24 is maximized. Complete or perfect utilization would be 100%, with no waste of the third sheet 84.

The pockets 86 may be formed by stamping, by die cutting, by laser cutting and by any alternative suitable forming method. The pockets 86 may, but need not, extend completely through the third sheet 84. The pockets 86 of the present example do extend completely through the third sheet 84, in part because the example third sheet 84 is substantially the same thickness T1 as the example cores 56.

The thermally conductive second material is formed into a plurality of the thermal transit cores 56. FIGS. 9 and 10 show twelve thermal transit cores 56 for the purpose of illustrating the concepts described herein, but this number can be varied to suit the manufacturing methods and equipment and the capabilities of such. One method of forming the cores 56 is to cut them from a sheet of thermally conductive material. A sheet (not shown) of thermally conductive material chosen as thermal transit core material, e.g., copper, aluminum, having an example thickness T1 of 0.23 mm, is provided. The cores 56 may be cut from the sheet into a desired shape and size. An example shape is shown in FIG. 6, with thickness T1 shown in the sectional view of FIG. 7. Cutting cores 56 from the sheet may be achieved by any commercially practicable method, with example methods including die cutting and laser cutting.

The thermal transit cores 56 may be placed into the pockets 86 of the third sheet 84. The relative sizes of the pockets 86 and the cores 56 may be selected to provide a press fit of the cores 56 into the pockets 86, or a slip fit to allow easy placement of the cores 56 within the pockets 86. The use of a slip fit may be better suited to use in arrangements in which the pockets 86 do not extend entirely through the third sheet 84, or in which the first sheet 92 of stainless steel, i.e., a stainless steel sheet 92, is fixed to a first surface 94 of the third sheet 84 prior to insertion of the cores 56, with the first sheet 92 defining a bottom to the pockets 86.

The first substantially planar sheet 92 is placed over a first surface 94 of the third sheet 84, in alignment therewith and is fixed to the third sheet 84. The third sheet 84 and the first sheet 92 may be connected by fixing, e.g., welding, adhesively bonding, the sheets 84, 92 together.

The second substantially planar sheet 90 is placed over a second surface 88 of the third sheet 84, the second surface 88 being opposite the first surface 94, in alignment therewith and is fixed to the third sheet 84. The third sheet 84 and the second sheet 90 may be connected by fixing, e.g, welding, adhesively bonding the sheets 84, 90 together.

The vertical flanking members 60 comprise part of the third sheet 84, connecting what will become inner parts of the proximal portion 34 and the distal portion 38 that are also comprised by part of the third sheet 84. Thus, the vertical flanking members 60 and the portions of the proximal portion 34 and the distal portion 38 formed of the third sheet 84 are formed as an integral unit.

The cores 56 are now trapped in a first direction between the first and second planar sheets 92 and 90 and in a second direction by the third sheet 84. Sheets 90 and 92 provide example horizontal flanking members 58 over the cores 56 in the finished saw blades 24. The horizontal flanking members 58 provided by the sheets 90 and 92 may additionally beneficially aid in the retention of the core 56 in the pocket 86 of the finished blade 24 during use of the blade 24.

In one alternative construction, the pockets 86 in the third sheet 84 do not extend completely through the third sheet 84. After the cores 56 have been disposed in the pockets 86, the cores 56 are retained therein by fixing the second sheet 90 over the third sheet 84 as described above. With the cores 56 so retained, there is no need for the first sheet 92.

In yet another alternative construction, the first and third sheets 92, 84 may be of equal thickness, e.g., 0.19 mm, with each having pockets 86 formed therein with a depth of each pocket 86 being of a depth substantially equal to one half the thickness T1 of the cores 56, e.g., 0.11 mm. The sheets 92, 84 are fixed together. The cores 56 are disposed in the pockets 86 of one of the sheets 92, 84. The second sheet 90 is then aligned with and lowered over and onto the third sheet 84. The sheets 84, 90 are then fixed to each other.

The assembled cores 56 and sheets 84, 90, 92 comprise the blank sheet assembly 96. A plurality of saw blade blanks 98, twelve in the illustrated example, may be cut from the blank sheet assembly 96. Profiles of the blade blanks 98 are shown on the blank sheet assembly 96 in phantom.

Figure 12C:
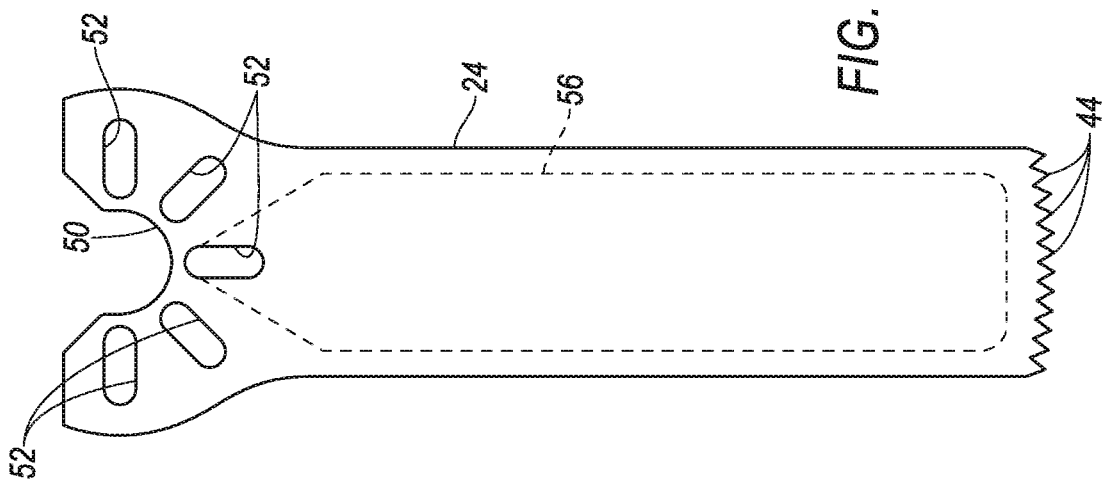
FIG. 12C is a top view of the example saw blade blank of FIGS. 12A and 12B in an example completed condition.
Figure 12B:
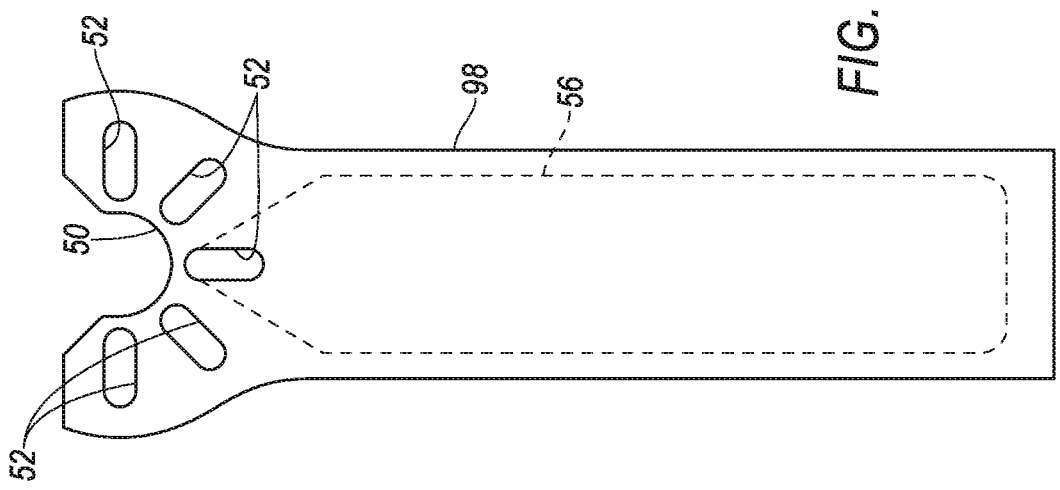
FIG. 12B is a top view of the example saw blade blank of FIG. 12A in an example intermediate condition.
Figure 12A:
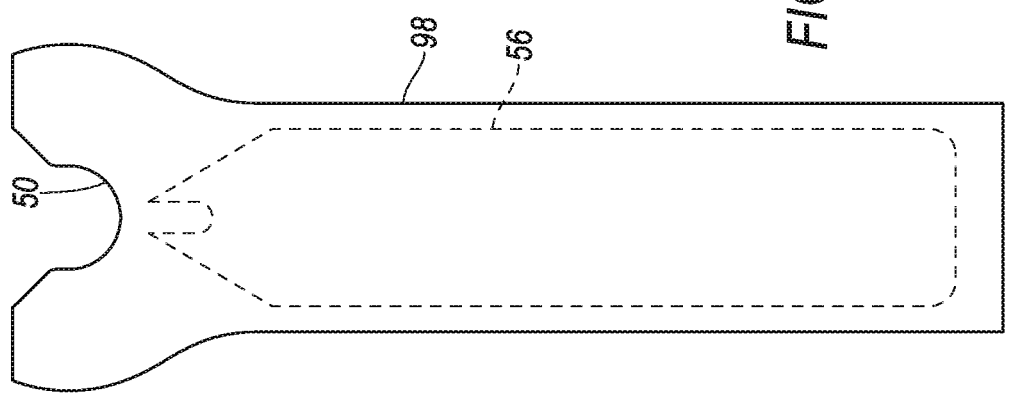
FIG. 12A is a top view of an example saw blade blank in an example first condition, as may be formed from the sheet assembly of FIGS. 10 and 11.

A blade blank 98 is shown in FIG. 12A, substantially as it would appear after being cut from the sheet assembly 96. The blade blank 98 may be further processed as indicated in FIGS. 12B and 12C to produce a completed blade 24. The blank 98 may have position-retention slots 52 formed by die cutting or other suitable material removal method to provide the partially finished blanks 98 of FIG. 12B. Such material removal may alternatively be performed when the blade blanks 98 are still part of the blank sheet assembly 96. The teeth 44 may be formed by cutting the edge 42. The teeth 44 may be ground and finish-ground to achieve their final shape and surface finish illustrated in FIGS. 12C and 3. The engagement arc 50 may be completely formed by the process in which the blade blank 98 is cut from the blank sheet assembly 96. The engagement arc 50 may alternatively be formed or formed in part by machining or grinding after the blade blank 98 is cut from the blank sheet assembly 96.

In yet another example of the method, not illustrated, the intermediate layer, including the first material and the second material, may be provided by an alternating plurality of parallel strips, i.e., ribbons, of the first material and the second material. Strips of the first material may be of a first width, substantially equal to at least a length of the distal portion 38 to accommodate forming blanks 98 having the distal portion 38 formed entirely of the first material. Alternatively, the strips of the first material may be wider, e.g., as wide as at least a combined length of the proximal portion and the distal portion, to accommodate forming blanks 98 having both proximal portions 34 and distal portions 38 formed substantially entirely of the first material. Strips of the second material may be of a second width substantially equal to a length of the proximal portion 34 and the body portion 46. The strips of the first material may be fixed, e.g., welded, adhesively bonded, to the opposing first and second sheets 92, 90. Blade blanks 98 are then cut from the assembled blank sheet assembly, with the sheets 92, 90 forming the horizontal flanking members 58. The blanks 98 are then processed into blades 24 in accord with the above.

An alternative method of forming the blades 24 may include the use of additive manufacturing methods, i.e., 3D printing. The blade 24 in its entirety by additive manufacturing. Or a blade blank 98 may be formed in its entirety by additive manufacturing and then finish machined. Or components of the blade blank, e.g., the core 56 may be formed by additive manufacturing and then incorporated into the blank sheet assembly 96. Or the components of the blade blank, e.g., the core 56, the flanking members 58, 62, the distal portion 38 and the proximal portion 34, may be formed separately or in combination and subsequently assembled.

In use, the completed blade 24 has its blade hub 30 inserted into, i.e., received by, and engaged by the blade mount 28. The blade 24 may be pivoted about an axis 100 of the mount 28. The axis 100 is substantially normal to a substantially planar surface 102 of the blade 24. The teeth 44 may be directed against a surgical site surface, e.g., a bone surface. The motion of the blade 24 relative to the surgical site surface and relative to the hand piece 22 causes the teeth 44 to sweep back and forth in a plane and across the bone, removing bone material from the bone, while cutting a slot with a kerf of a width substantially equal to the blade thickness TS.

The energy from a motor (not shown) in the hand piece 22 is, in large part, transferred to the teeth 44 to cut the bone. Heat generated at a cutting site, where the teeth 44 are removing bone, is conducted by the blade 24 away from the teeth 44 and toward the mount 28. The rate of heat conduction through the core 56 is greater and more rapid than the rate through steel, allowing the saw blade 24 with its thermal transit core 56 to operate at a lower temperature than a conventional steel blade. The transfer of heat away from the teeth 44 through the blade 24 is facilitated by heat transfer mechanisms including conduction through the core, radiation and convection. Heat is lost by the blade 24 and the core 56 across the length L1 of the blade's thermal transit core 56 to the surrounding air by both convection and radiation, in combination with conduction. The core 56 conducts heat along the length L2 of the blade, with some of the heat being conducted through the comparatively thin layer of steel defining the horizontal flanking member 58 to the surface 102 of the blade to the surrounding environment, e.g., air. Heat passing though the layer of steel 58 to the outer surface 102 of the blade will be dissipated by radiation, and by convection as air moves across the outer surface 102 of the blade.

Heat is also conducted through the core 56 to the mount 28. Conduction of heat through the blade 24 away from the teeth may be further facilitated by providing the heat sink 32, 32' at the mount 28. Removal of heat from the heat sink 32, 32' enhances removal of heat from the blade 24 and from the cutting site.

Tests conducted demonstrated that an average temperature of the teeth 44 of a commercially available steel blade cutting a piece of wood was 134 degrees Celsius at the end of a predetermined cutting cycle. With the disclosed blade 24 incorporating the copper core 56 cutting a piece of wood under identical conditions, the average temperature of the teeth of the blade 24 was 72 degrees Celsius at the end of the cutting cycle. Given an ambient temperature of 21 degrees Celsius, the temperature increase of the blade teeth relative to ambient was reduced by 55% when using the disclosed blade instead of a commercially available steel blade. The blade 24 used in the test was substantially consistent with the above description. In both tests, the blade mount used was a commercially available mount and did not include a supplemental heat sink of either the passive or active type. The lower temperatures may allow cutting that may otherwise employ cooling irrigation to be performed without cooling irrigation, avoiding challenges, e.g., reduced site visibility, that may be presented by the use of cooling irrigation.

FIGS. 13 through 16 show example alternative surgical saw blades 24' and 24". Like reference numbers (e.g. 24 and 24' and 24") identify like parts and features, subject to the described distinctions.

Figure 13:
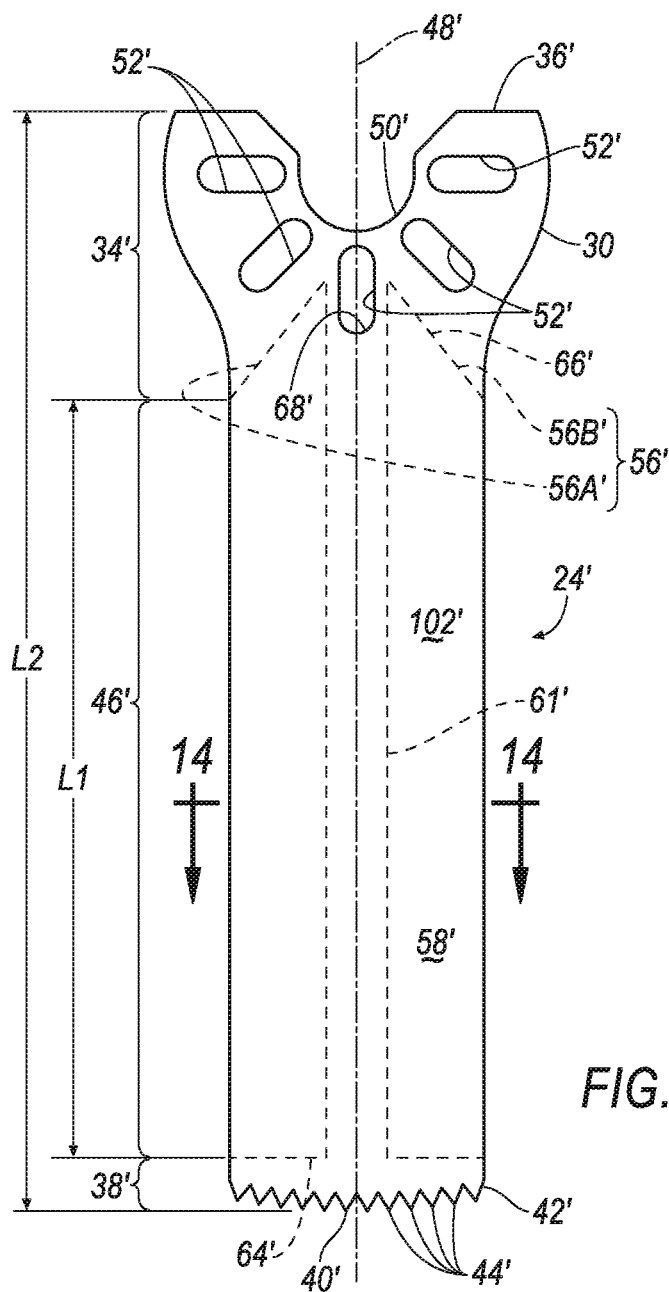
FIG. 13 is a top view of an alternative example surgical saw blade of the example saw system of FIGS. 1 and 2.
Figure 14:
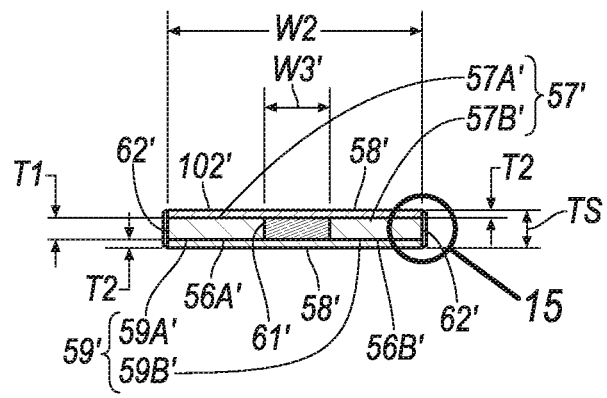
FIG. 14 is a sectional view of the saw blade of FIG. 13 taken in the direction of arrows 14.

FIGS. 13, 14 and 15 show the example alternative example surgical saw blade 24' in greater detail. The saw blade 24' is much like the blade 24, except that the saw blade 24' includes a longitudinal beam 61' and does not include flanking members 60.

A proximal portion 34' of the blade 24', disposed at a proximal end 36' of the blade 24', includes a blade hub, e.g., blade hub 30 or blade hub 30'. A distal portion 38' of the blade 24', disposed at a distal end 40' of the blade 24', includes the cutting edge 42'. The cutting edge 42' may include the cutting teeth 44'. A body portion 46' is disposed between and connects the proximal portion 34' and the cutting edge 42' of the distal portion 38'. The longitudinal axis 48 extends from the proximal end 36' to the distal end 40', substantially bisecting the blade 24'. The saw blade 24' may be substantially symmetrical about the axis 48, with opposing sides of the blade 24' across the axis 48 being substantially a mirror image of the other. The blade 24' and its body portion 46', as shown in FIGS. 13 and 14, are substantially planar. As with the blade 24, the body portion 46' of the blade 24' may have a length L1' comprising more than half a length of the saw blade L2'.

As with the blade 24, the distal portion 38', and thus the cutting edge 42' and the teeth 44' of blade 24', may be formed of the above-described first material.

The proximal portion 34' may be formed of the same material as the distal portion 38', i.e., the first material. The illustrated proximal portion 34' is substantially the same as the proximal portion 34, and includes a blade hub 30 that includes an engagement arc 50' and a plurality of position-retention slots 52'. As noted above, the configuration of the blade hub is exemplary.

The body portion 46' includes a thermal transit core 56' that may be formed of the above-described second material, e.g. copper, aluminum, composites, having a second thermal conductivity greater than the first thermal conductivity. The thermal transit core 56' may be substantially bisected into a first half 56A' and a second half 56B' by the longitudinal beam 61'. The longitudinal beam 61' may be formed of the same material as the distal portion 38'. The longitudinal beam 61' may extend between and connect the proximal portion 34' and the distal portion 38'. The longitudinal beam 61' may further be of an example third width W3' substantially narrower than the width W2 of the blade. The width W2 may be 9 mm as described above. An example width W3' may be 2 mm. The body portion 46' may also include a pair of opposed of horizontal flanking members 58'. The flanking members 58' may extend longitudinally, i.e., extend in the direction of the longitudinal axis 48, from the proximal portion 34' across the body portion 46' to the distal portion 38', or may alternatively be disposed over and comprise part of each of the proximal portion 34' and the distal portion 38'.

One of the horizontal flanking members 58' may be disposed across an upper horizontal surface 57', comprising surfaces 57A' and 57B' of the core halves 56'A and 56B' respectively, and over the beam 61'. The opposed horizontal flanking members 58' may be disposed across a lower horizontal surface 59' of the core 56', the lower horizontal surface 59' comprising surfaces 59A' and 59B' of the core halves 56A' and 56B' respectively, and over the beam 61'. The upper horizontal surface 57' and the lower horizontal surface 59' of the core 56' each extend longitudinally an entire length of the core 56'. The upper horizontal surface 57' and the lower horizontal surface 59' as illustrated in FIG. 7 are connected with each other on opposed sides by two oppositely disposed vertical surfaces 62' of the core 56'. The vertical surfaces 62' also extend longitudinally along the length of the core 56' and may be exposed, permitting contact therewith.

The beam 61' and inner parts of the proximal portion 34 and the distal portion 38 may be formed as a single integral piece.

The body portion 46' may be provided with a biocompatible surface. When the core 56' is formed of a non-biocompatible material, the layer forming the biocompatible surface may be provided by disposing the horizontal flanking members 58' over the upper horizontal surface 57', and over the lower horizontal surface 59'. When, as in FIGS. 13-15, the vertical surfaces 62' of the core 56' would otherwise be exposed, i.e., uncovered by vertical flanking members, a thin surface layer 72' of biocompatible material, e.g., aluminum oxide, anodized aluminum, polymeric coatings, gold, titanium nitride, may be applied. Such a surface layer 72' when so formed may be relatively thin (e.g., 0.01 mm), and thus may not substantially impact the ultimate width W2 of the blade 24'.

Figure 16:
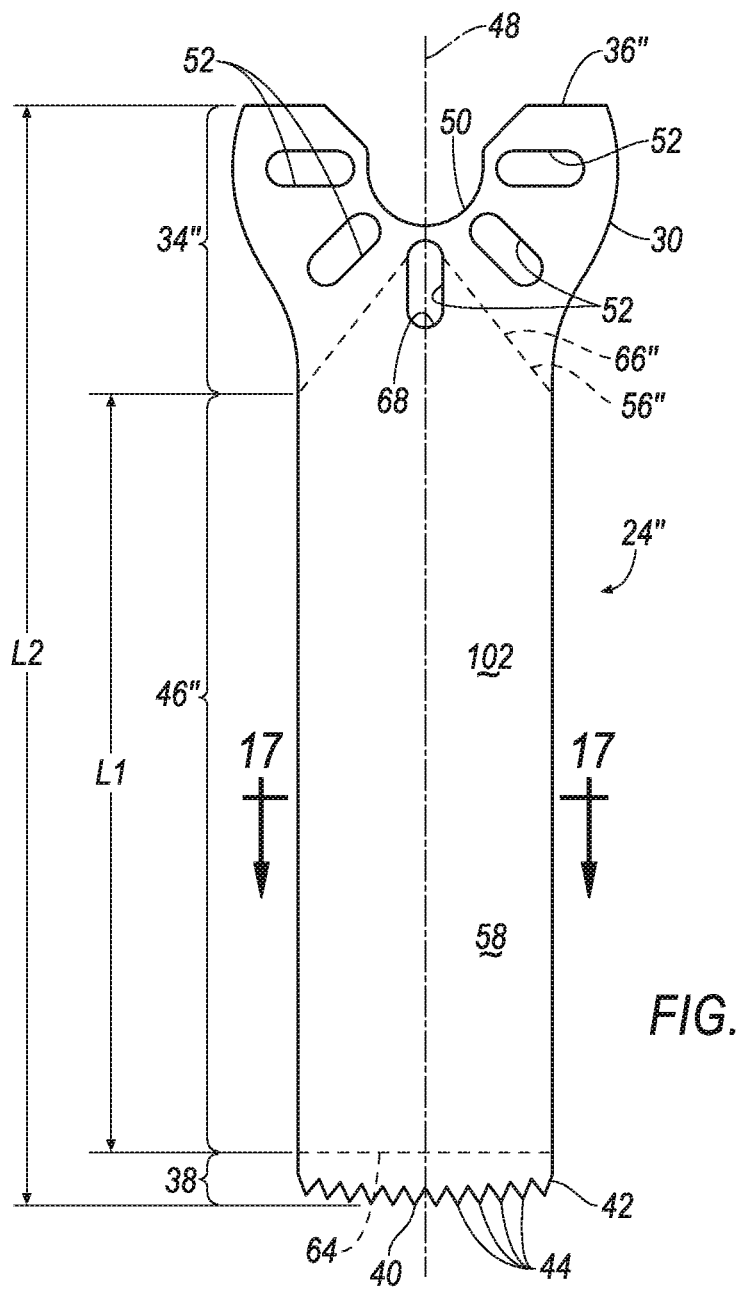
FIG. 16 is a top view of another alternative example surgical saw blade of the example saw system of FIGS. 1 and 2.
Figure 17:
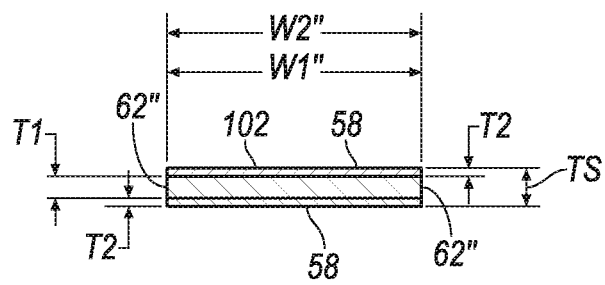
FIG. 17 is a sectional view of the saw blade of FIG. 16 taken in the direction of arrows 17.

FIGS. 16 and 17 show the example alternative surgical saw blade 24" in greater detail. The saw blade 24" is much like the blade 24, except that the width W1" of the core 56" is equal to the full width W2" of the saw blade 24" and the width W2" of the opposed horizontal flanking members 58. Vertical flanking members 60 are not employed in the saw blade 24". An example width W1" may be 9 mm and an example width W2" may be 9 mm. A distal edge 64 of the core 56" is engaged by the distal portion 38 of the blade 24". A proximal end 66" of the core 56" may extend into the blade hub 30" to aid in a transfer of heat from the teeth 44 as described above. Vertical surfaces 62" may be provided with a layer 72' to provide a biocompatible surface 72' as described above and as shown in FIG. 15.

A surgical saw blade, a blade thermal management system and a method for making the surgical saw blade have all been disclosed. The disclosed blade facilitates an improved surgical saw system facilitating improved surgical efficiency in that for a given tooth pitch and profile, cutting may be done at a higher rate of speed for a predetermined temperature at the cutting site, and improved precision in that a blade with a finer tooth pitch may be used to cut at the same rate of speed as a less precise blade having a coarser tooth pitch while not exceeding the predetermined temperature.

In the drawings, the same reference numbers indicate the same elements. Further, some or all of these elements could be changed. With regard to the media, processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

As used herein, the adverb "substantially" means that a shape, structure, measurement, quantity, time, etc. may deviate from an exact described geometry, distance, measurement, quantity, time, etc., because of imperfections in materials, machining, manufacturing, transmission of data, computational speed, etc.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A surgical saw blade comprising:
    a cutting edge including a plurality of teeth substantially entirely formed of a first material having a first thermal conductivity;
    a proximal portion including a blade hub; and
    a body portion disposed between and connecting the cutting edge and the proximal portion and including:
        a thermal transit core formed of a second material having a second thermal conductivity at least twice the first thermal conductivity and the core having at least two opposed longitudinally extending first core surfaces extending across a width of the core, and
        at least two opposed longitudinally extending first flanking members respectively disposed over the longitudinally extending first core surfaces.

2. The surgical saw blade of claim 1 wherein the cutting edge is formed of steel and the longitudinally extending first flanking members are formed of steel.

3. The surgical saw blade of claim 1 wherein the cutting edge is formed of steel and the proximal portion is formed substantially entirely of steel.

4. The surgical saw blade of claim 1 wherein the cutting edge is disposed at a distal end of the blade and the cutting edge is formed of steel.

5. The surgical saw blade of claim 1 wherein the cutting edge is disposed at a distal end of the blade and the saw blade is substantially symmetrical about a longitudinal axis extending from the blade hub to the teeth.

6. The surgical saw blade of claim 1 wherein steel sheets are disposed over the first core surfaces to provide the flanking members.

7. The surgical saw blade of claim 1 wherein the cutting edge is formed of steel and two opposed second flanking members are formed of steel and are connected to the first flanking members and extend along each of two opposed second core surfaces extending across a thickness of the thermal transit core.

8. The surgical saw blade of claim 1, wherein:
the cutting edge is located on a distal end of the saw blade opposite the blade hub,
the body portion comprises more than half of a length of the saw blade, and
the surgical saw blade, including the proximal portion and the cutting edge and the body portion, is substantially planar and of a substantially constant thickness.

9. The surgical saw blade of claim 1 wherein the thermal transit core substantially comprises copper.

10. The surgical saw blade of claim 1 wherein the thermal transit core substantially comprises aluminum.

11. A method of making a surgical saw blade comprising the steps of:
forming layers of a blank sheet assembly, the layers including:
a substantially planar first sheet of steel of a first thickness and having a first planar area,
a substantially planar second sheet of steel having a second planar area substantially equal to the first planar area and having a second thickness substantially equal to the first thickness, and
an intermediate layer disposed between the first sheet and the second sheet, the intermediate layer including both steel incorporated into cutting edges and a second material having a thermal conductivity greater by at least a factor of two than the thermal conductivity incorporated into a thermal transit core in blades formed;
fixing the first and second sheets to opposite sides of the intermediate layer to form the blank sheet assembly;
cutting a plurality of saw blade blanks from the blank sheet assembly with each blank having a thermal transit core formed of the second material and a cutting edge formed of steel;
forming a blade hub in a proximal end of the blade blanks; and
forming cutting teeth on the cutting edge of the blade blanks.

12. The method of claim 11, wherein the steel of the intermediate layer is provided as a third sheet of steel including a plurality of regularly disposed pockets of a predetermined shape and size formed therein and the second material is provided as a plurality of thermal transit cores of substantially the same size and shape as the pockets, and further comprising the step of disposing the thermal transit cores in the pockets of the third sheet.

13. The method of claim 11, wherein the steel of the intermediate layer also comprises at least part of the proximal end.

14. The method of claim 11, wherein the first and second steel sheets are welded to the steel of the intermediate layer.

15. The method of claim 11, wherein the second material substantially comprises copper.

16. A surgical saw blade comprising:
a distal portion including a cutting edge with a plurality of teeth substantially entirely formed of a first material having a first thermal conductivity;
a proximal portion including a blade hub; and
a body portion disposed between and connecting the distal portion and the proximal portion and including:
a thermal transit core formed of a second material having a second thermal conductivity at least twice the first thermal conductivity and the core having at least two opposed longitudinally extending first core surfaces extending across a width of the core, and
a pair of opposed vertical flanking members made from a stiffer material than the second material of the thermal transit core, the vertical flanking members extending longitudinally from the proximal portion across the body portion to the distal portion.

17. The surgical saw blade of claim 16, wherein vertical flanking members and inner parts of the proximal portion and the distal portion are formed as an integral unit.

18. The surgical saw blade of claim 16, wherein the thermal transit core comprises a plurality of surfaces which include an upper horizontal surface, a lower horizontal surface, and two vertical surfaces.

19. The surgical saw blade of claim 18, wherein the vertical flanking members extending longitudinally across one of the vertical surfaces of the thermal transit core.

20. The surgical saw blade of claim 18, wherein one of the vertical flanking members is disposed across one of the vertical surfaces of the thermal transit core, and another of the vertical flanking members is disposed across the opposed vertical surface of the thermal transit core.

21. The surgical saw blade of claim 18, further comprising horizontal flanking members, one of the horizontal flanking members disposed across the upper horizontal surface of the thermal transit core, and another of the horizontal flanking members disposed across the lower horizontal surface of the thermal transit core.

22. The surgical saw blade of claim 16, wherein the vertical flanking members are formed from one of a series 300 or 400 stainless steel, tungsten carbide, or titanium.

23. The surgical saw blade of claim 16, wherein the vertical flanking members are formed from a biocompatible material.

24. The surgical saw blade of claim 16, wherein the thermal transit core substantially comprises one of copper or aluminum.

* * * * *